United States Patent
Trahan et al.

(10) Patent No.: US 9,021,884 B2
(45) Date of Patent: *May 5, 2015

(54) SENSOR FOR HIGH PRESSURE PROCESSING OF ARTICLES

(71) Applicant: Del Monte Foods, Inc., San Francisco, CA (US)

(72) Inventors: Caitlin Elizabeth Trahan, Oakland, CA (US); Justin Wade Shimek, San Ramon, CA (US); Russel Allan Lem, Concord, CA (US); Andrew Richard Hart, Ithaca, NY (US)

(73) Assignee: Del Monte Foods, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,381

(22) Filed: Oct. 21, 2013

(65) Prior Publication Data

US 2014/0216162 A1    Aug. 7, 2014

Related U.S. Application Data

(63) Continuation of application No. 13/230,382, filed on Sep. 12, 2011, now Pat. No. 8,640,546.

(51) Int. Cl.
*G01L 7/00* (2006.01)
*G01L 7/08* (2006.01)
(Continued)

(52) U.S. Cl.
CPC . *G01L 7/00* (2013.01); *G01L 7/187* (2013.01); *A23L 3/00* (2013.01); *A23L 3/003* (2013.01); *A23L 3/0155* (2013.01); *A61L 2/28* (2013.01); *B01J 13/00* (2013.01)

(58) Field of Classification Search
None
See application file for complete search history.

(56) References Cited

U.S. PATENT DOCUMENTS

| 3,447,945 A | 6/1969 | Mishima et al. |
| 4,002,060 A | 1/1977 | Ogata et al. |

(Continued)

FOREIGN PATENT DOCUMENTS

EP    2 116 481 A1    11/2009

OTHER PUBLICATIONS

Minerich, Phillip L. and Labuza, Theodore P. "Development of a pressure indicator for high hydrostatic pressure processing of foods" P. Minerich, T. Labuza in Innovative Food Science Emerging Technologies (2003); http://www.sensorprod.com/news/white-papers/dpi/index.php.

(Continued)

*Primary Examiner* — Peter Macchiarolo
*Assistant Examiner* — Jermaine Jenkins
(74) *Attorney, Agent, or Firm* — Dilworth Paxson LLP

(57) ABSTRACT

A pressure sensor device and its use for confirming achievement of a selected pressure in a high pressure process (HPP) for sanitizing food is disclosed. The device includes at least a base and a sheet, each of which is substantially impermeable to the working fluid of the HPP and is deformable at the selected pressure. Microcapsules interposed between flat overlapping portions of the base and sheet contain a color former and burst upon pressurization of the environment surrounding the device. Release of the color former is detected to confirm that the pressurization occurred. The device can be associated with one or more foodstuffs (e.g., a packaged food product or a group of such packages) and remain associated therewith to continuously indicate that the foodstuff(s) have been subjected to the selected pressure and are therefore sanitized.

18 Claims, 5 Drawing Sheets

(51) Int. Cl.
*G01L 7/18* (2006.01)
*A23L 3/00* (2006.01)
*A23L 3/015* (2006.01)
*A61L 2/28* (2006.01)
*B01J 13/00* (2006.01)

(56) References Cited

U.S. PATENT DOCUMENTS

| | | |
|---|---|---|
| 4,078,423 A | 3/1978 | Ogata et al. |
| 4,098,114 A | 7/1978 | Asao et al. |
| 4,761,397 A | 8/1988 | Higashi et al. |
| 6,562,117 B2 * | 5/2003 | Sano et al. ............ 106/31.6 |
| 6,799,467 B2 | 10/2004 | Minerich et al. |
| 6,805,046 B1 * | 10/2004 | Rasmussen ............ 101/33 |
| 2011/0138924 A1 * | 6/2011 | Colombo et al. ............ 73/756 |

OTHER PUBLICATIONS

"Tactile Pressure Indicating Sensor Film", Pressurexs ®, ©2010 Sensor Products Inc.; Updated Jan. 4, 2010.

\* cited by examiner

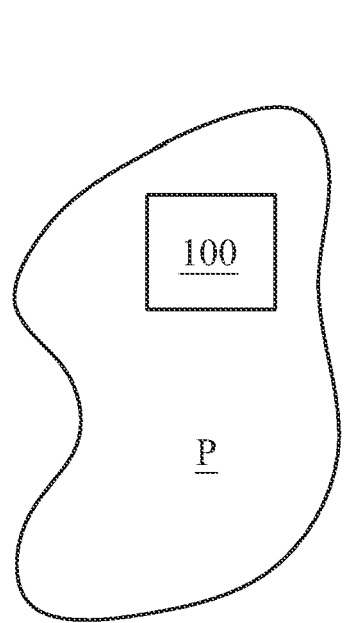
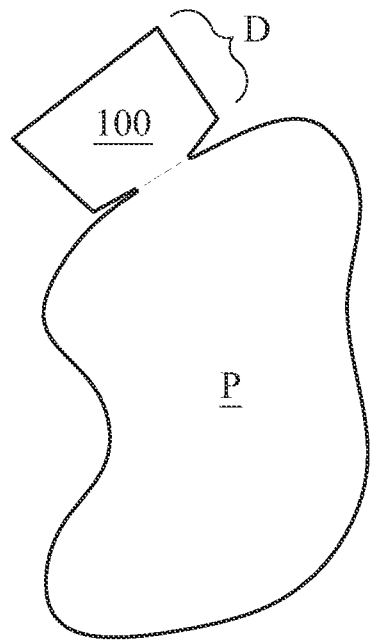
FIG. 6A  FIG. 6B
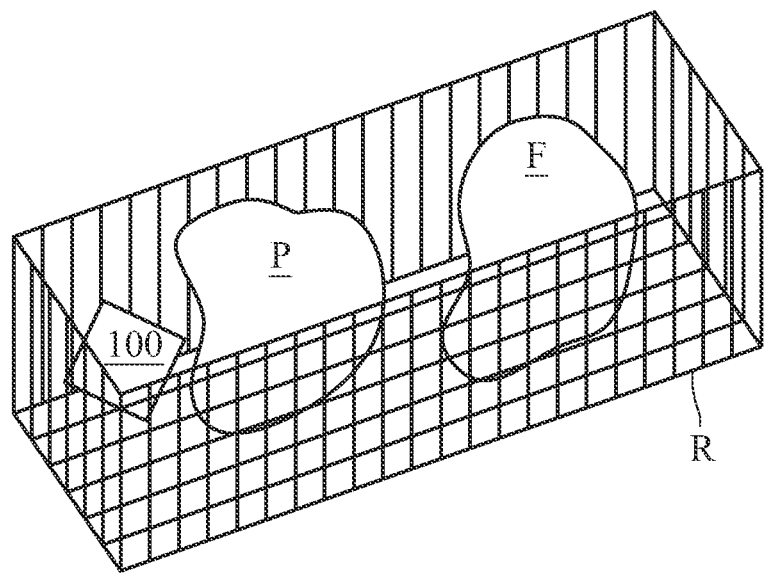
FIG. 7A

SENSOR FOR HIGH PRESSURE PROCESSING OF ARTICLES

CROSS-REFERENCES TO RELATED APPLICATIONS

This application is a continuation of U.S. application Ser. No. 13/230,382 (now U.S. Pat. No. 8,640,546) which was filed on 12 Sep. 2011.

FIELD OF THE DISCLOSURE

The disclosure relates generally to the field of high pressure processing of articles for the purpose of mitigating or eliminating the risk of microbial growth in or on an article.

BACKGROUND OF THE DISCLOSURE

High pressure processing (HPP), also known as high hydrostatic pressure processing, pascalization, and bridgmanization, is a technique whereby articles such as food items are subjected to pressure of an intensity and for a duration of time sufficient to reduce the biological activities of cells and their components, thereby decreasing the likelihood that cells subjected to such processing will continue to metabolize or reproduce. As such, HPP techniques can be used to mitigate or eliminate the risk that bacteria, mold, yeast, and parasites will survive or multiply in or on HPP-treated articles.

Foodstuffs intended for human or other animal consumption are susceptible to microbial contamination, especially during handling and processing, and such contamination can continue and increase during storage. Furthermore, natural components (e.g., endogenous enzymes) in foodstuffs such as vegetables, fruits, and meats can exert degradative effects upon the foodstuff during storage, even in the absence of microbial contamination. A continuing need exists for methods of reducing spoilage and degradation of foodstuffs during storage. HPP methods have been widely investigated and reported. Their efficacy for reducing the risk of contamination of foodstuffs and thereby extending the period for which foodstuffs can practically be stored has been demonstrated by others.

In HPP techniques, food or other articles are often sealed in a container prior to subjecting the sealed container to high pressure, such as 200-1000 megaPascals (MPa; more typically 200-600 MPa). Because gases are highly compressible at such pressures, some or substantially all gases can be removed from the container prior to sealing it, such as by evacuating gases from the container or by filling the container with liquid prior to sealing it. Liquids and solids, being relative incompressible at these pressures, tend to transmit pressure throughout their volume, provided there are no rigid articles present (e.g., thick, hollow bones or shells capable of preventing transmission of isotropically applied pressure to their interior). Pressure can be applied to the exterior of the article or the exterior of the container containing the article and transmitted throughout the article. In practice, pressurization is often achieved in a sturdy device designed for accommodating one or more articles during such pressurization. Pressurization devices often have controls for selecting the pressure and the duration of pressurization and indicators for indicating the pressure achieved and/or the duration of the pressurization process.

HPP processes do not require heating of the treated article, although heat can be applied, for example to inactivate spores or other heat-labile components that can be expected to be unaffected by HPP processing.

Following HPP treatment, non-compressible articles such as liquid foods (e.g., soups and juices) often appear similar to or indistinguishable from non-treated articles of the same type. Although failure of HPP treatment to alter the outward appearance of an article may be beneficial in some respects (e.g., that treated foods may look identical to fresh, untreated foods), the lack of apparent changes can lead to confusion among HPP-treated and -non-treated articles. In an environment, such as a food processing facility, in which non-treated articles can be expected to be in close proximity to non-treated articles, the appearance of the articles alone can be an insufficiently reliable indicator of HPP treatment status to prevent an operator from mistaking a non-treated article for an HPP-treated article. Likewise, because pressurization equipment can sometimes fail to achieve the degree or duration of pressurization desired by its operator, and such failures can be difficult for an operator to perceive. For articles that fail to undergo an alteration in their appearance during HPP processing, such failures may go undetected and insufficiently processed articles can be mistaken for appropriately processed ones.

It would be beneficial if an indicator could be associated with an article intended to be subjected to HPP, the indicator undergoing a readily-observable change of appearance upon HPP and not undergoing the change absent HPP.

Others have recognized the need for such an indicator.

By way of example, U.S. Pat. No. 6,799,467 to Minerich et al. discloses a tablet formed from powdered metal that is capable of undergoing a change in density upon HPP. A potential drawback of such a tablet, however, is that determining a change in tablet density can be difficult and time-consuming to detect, and outward changes in the tablet may not be readily discernable.

Further by way of example, European Patent Application publication no. 2116481 discloses an irreversible pressure-sensitive marker in which pigment-containing microcapsules are disposed between a rigid base member and a transparent film. When subjected to HPP, the rigid base member retains its shape and anisotropic force is applied to the microcapsules by the transparent film, resulting in rupture of the microcapsules, escape of the hitherto-contained pigment, and visibility of the pigment through the film. In view of the high pressures used during HPP and the corresponding expense of providing a rigid base member capable of retaining its shape under such pressures so as to exert anisotropic force upon the microcapsules, such a system can be economically impractical for common use.

Disclosed herein is a sensor and method of using it that can be associated with an article to be subjected to HPP. The sensor undergoes a readily-observable change of appearance upon HPP and does not require a rigid base member.

Figure 3A:
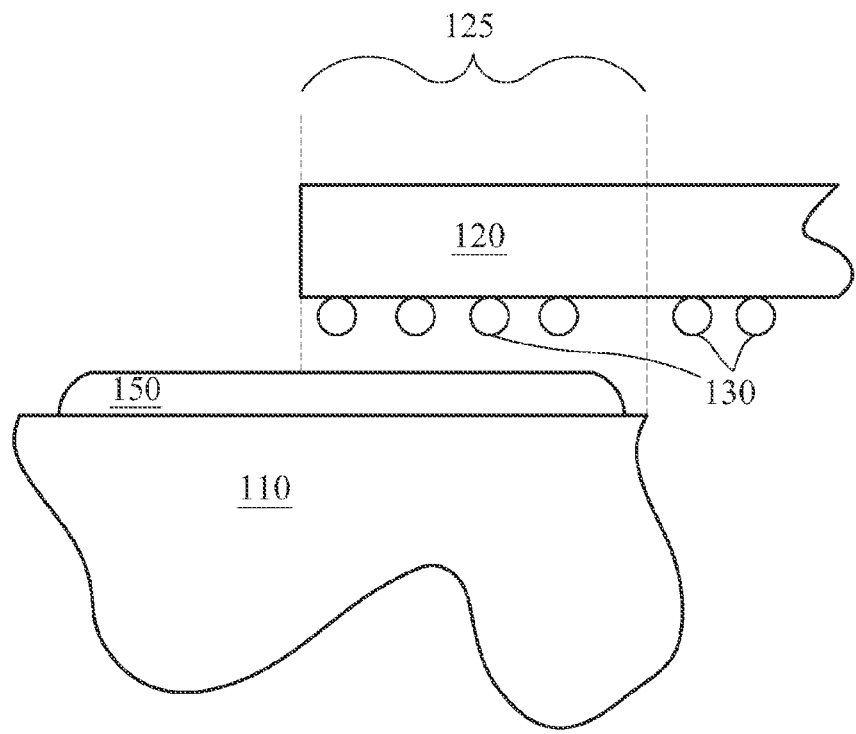
Figure 3B:
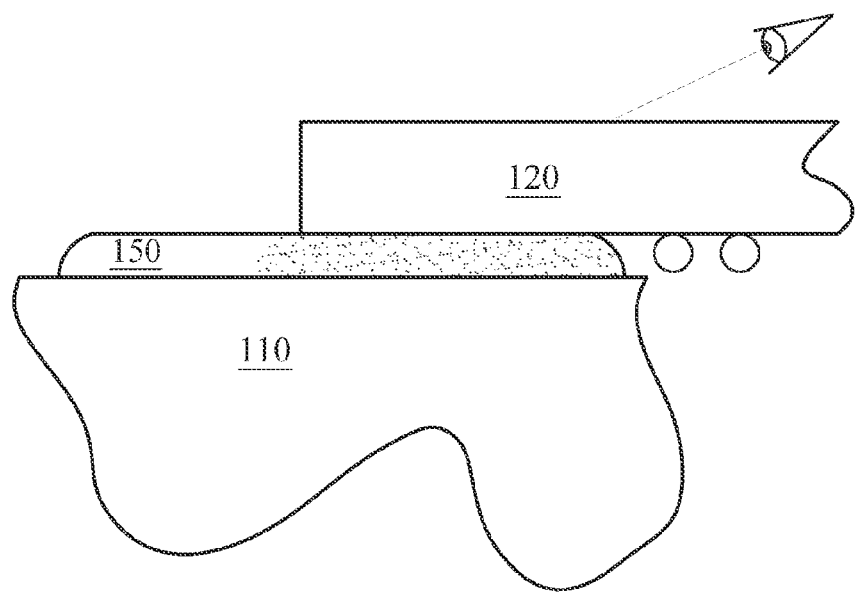

FIG. 3 consists of FIGS. 3A and 3B, each of which is a cross-sectional diagram illustrating operation of the device described herein. FIG. 3A illustrates the arrangement of elements prior to increasing the ambient pressure to or above a selected value. In FIG. 3A, microcapsules 130 containing a color former are bound to a sheet 120 that overlaps a portion of a base 110 in an overlapping portion 125. The base 110 is coated with a layer of a color developer 150 that reacts with the color former to form a colored product. FIG. 3B illustrates the arrangement of elements in the device shown in FIG. 3A after increasing the ambient pressure to or above a selected value. In FIG. 3B, color former released from crushed microcapsules has penetrated into color developer 150 layer to form a colored product, which can be viewed by observing the exterior of the device, since sheet 120 is transparent in this embodiment.

Figure 4A:
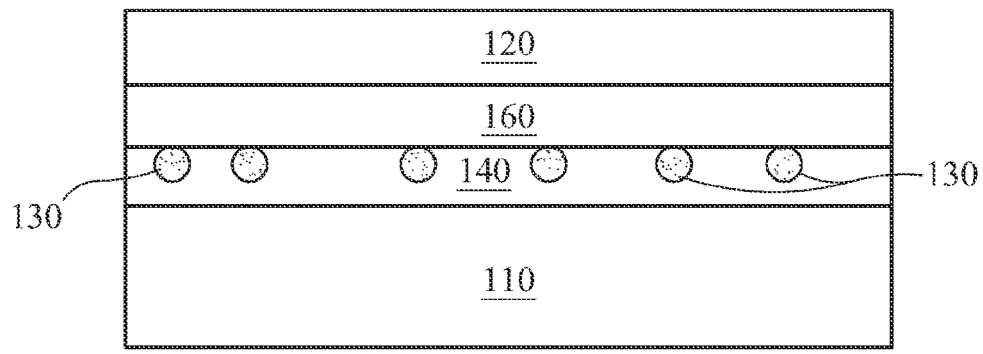
Figure 4B:
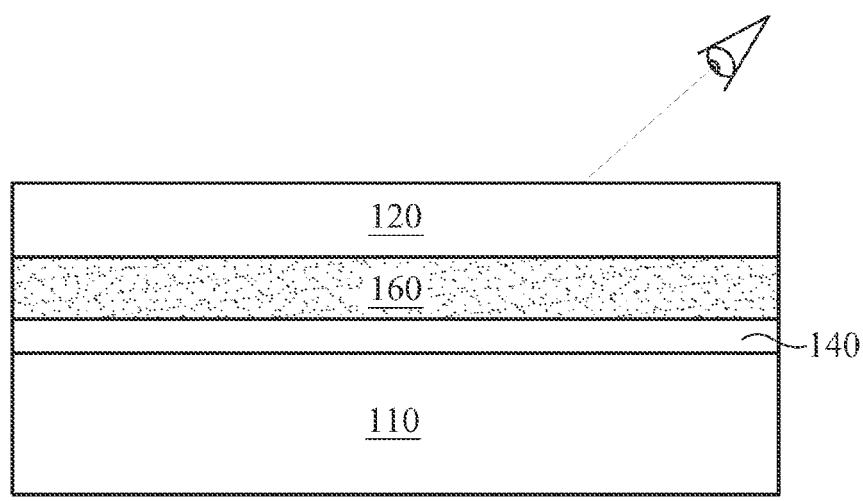

FIG. 4 consists of FIGS. 4A and 4B. FIG. 4A illustrates the arrangement of elements prior to increasing the ambient pressure to or above a selected value. In FIG. 4A, microcapsules 130 containing a color former are contained within a layer of binder 140 that is bound to a base 110 that can be transparent, translucent, or opaque. An absorbent material 160 having an initial color is interposed between the layer of binder 140 and a transparent sheet 120. FIG. 4B illustrates the arrangement of elements in the device shown in FIG. 4A after increasing the ambient pressure to or above a selected value. In FIG. 3B, color former released from crushed or compressed microcapsules has penetrated into absorbent material 160, altering its color. The color of the absorbent material 160 can be viewed by observing the exterior of the device.

Figure 5:
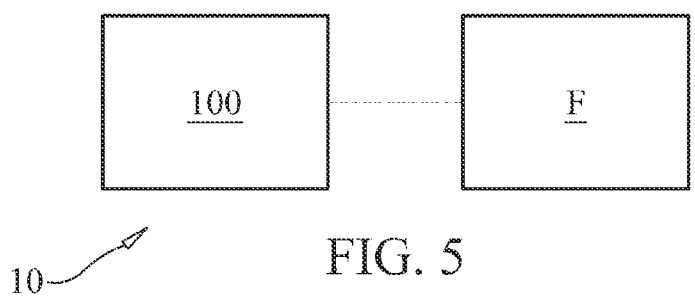

FIG. 5 is a diagram that conceptually illustrates the assembly described herein. In the assembly 10, a pressure sensor device 100 as described herein is reliably associated with a foodstuff F. The assembly 10 can be subjected to an HPP regimen without dissociating the device 100 from the foodstuff F.

FIG. 6 consists of FIGS. 6A and 6B and illustrates methods of reliably associating the device 100 described herein with a package P, such as one containing a foodstuff. In FIG. 6A, the device 100 is attached to the exterior of the package P (although it can, alternatively, be attached to the interior surface of the package P if the surface material is transparent); the device 100 can be viewed by direct visual observation of the exterior of the package, and can, optionally, be removable from the package P. In FIG. 6B, the device 100 is attached to a detachable portion D of the package P. The device 100 can be detached from the package P by detaching detachable portion D.

Figure 7B:
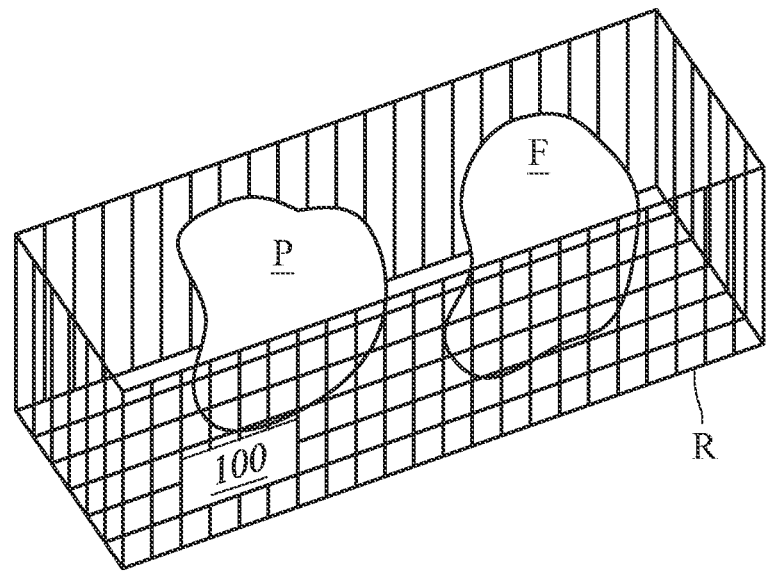
Figure 7C:
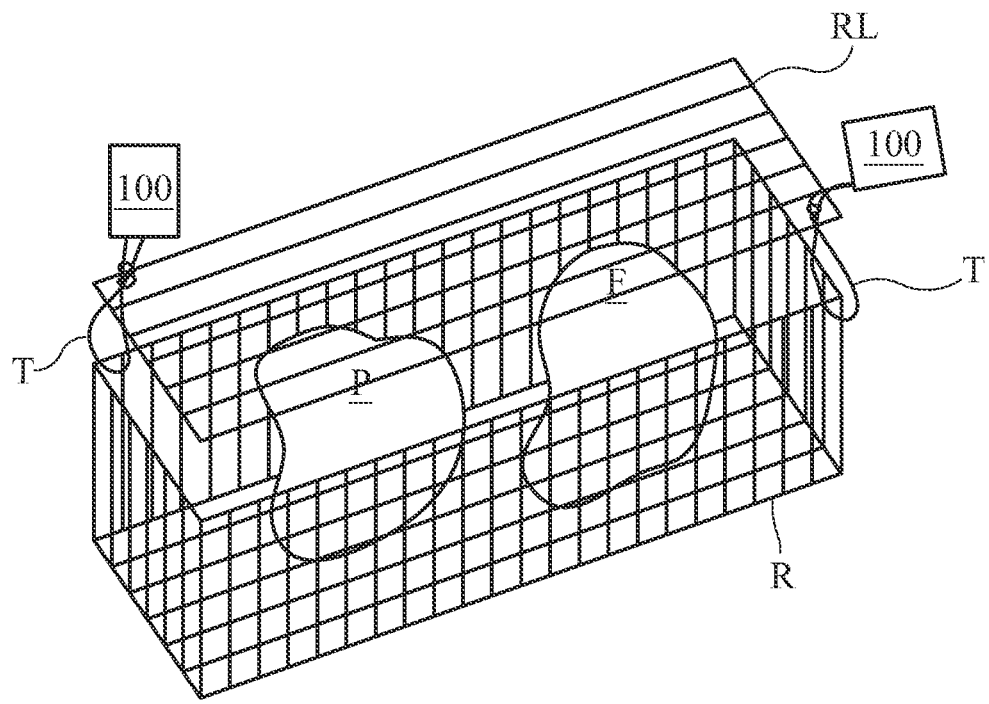

FIG. 7 consists of FIGS. 7A, 7B, and 7C and illustrates reliable association of a device 100 described herein with a rack R that supports or contains one or more packages P and/or foodstuffs F. In FIG. 7A, the device 100 is simply placed within the same rack R as are the package P and/or foodstuff F. in FIG. 7B, the device 100 is attached to the rack R into which the package P and/or foodstuff F are placed. In FIG. 7C, the package P and/or foodstuff F are placed within the rack R, and a rack lid RL is secured to the rack R using ties T that cannot be untied without removing device 100 from the tie T. In the embodiment shown in FIG. 7C, the package P and/or foodstuff F cannot be removed from the rack R unless the rack lid RL is removed, and the rack lid RL cannot be removed without manipulating at least one of the ties T to which a device 100 is attached; thus, the likelihood that an operator will observe at least one device 100 prior to removing the package P and/or foodstuff F is increased.

DETAILED DESCRIPTION

The disclosure relates to devices 100 for detecting and signaling that a desired pressure has been achieved within a vessel such as a food-processing vessel. In a particularly desirable application, the vessel is a pressurization vessel used in high pressure processing (HPP) methods of reducing the threat posed by microbial food contamination.

HPP food-processing methods are well known and described by others. Although HPP methods are known to be effective for enhancing the microbial safety of treated food products, they have the significant drawback that HPP-treated food items often have the same appearance before and after HPP treatment. Failure or improper operation of HPP equipment can yield foodstuffs that have the appearance of HPP-treated foodstuffs, even though they have not been so treated. One storing or using apparently-but-not-treated foodstuffs may fail to appreciate the microbial risk present in the foodstuffs, potentially resulting in serious illness, injury, or death. For this reason, stringent attention is often paid to product traffic control in HPP methods, to ensure that the HPP-treatment status of food products is accurately monitored. Such traffic control methods impose significant effort and expense, and can nonetheless fail to ensure that appropriate contamination-reduction methods have been employed. What is needed is an indicator device that can accompany foods throughout a HPP treatment regime (i.e., such that the device undergoes the same treatment as the foods) and indicate whether the desired pressure was achieved in the vessel containing the foods and indicator. This disclosure provides such indicators and methods of using them.

Figure 1:
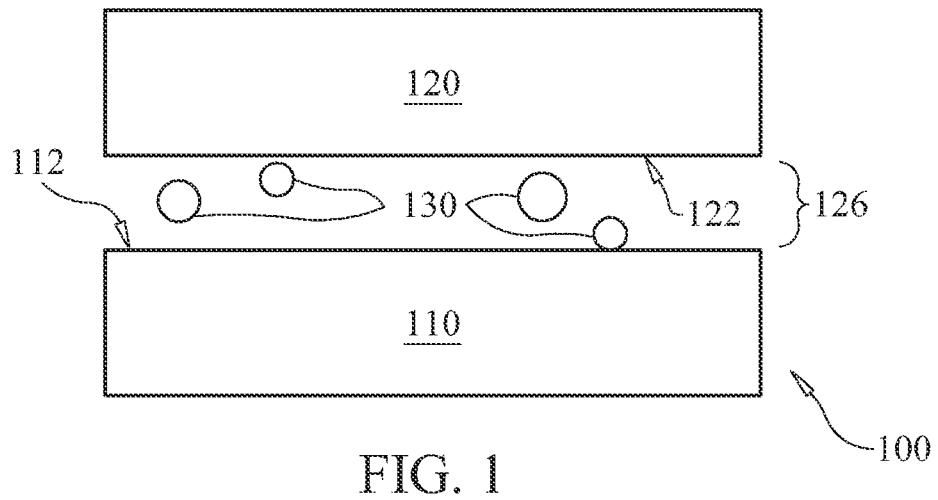
FIG. 1 is a cross-sectional diagram that illustrates the general arrangement of elements in the pressure sensor device 100 described herein. Microcapsules 130 are disposed between an opposable (in this embodiment, substantially flat) portion 112 of a base 110 and an opposable (in this embodiment, substantially flat) portion 122 of a sheet 120.

Simply summarized, and as shown in FIG. 1, the device 100 described herein has multiple microcapsules 130 contained between matching (preferably flat) portions of two bodies that can be urged together by ambient pressure and rupture of the microcapsules 130 is detectable, such as by observing release of a color former from ruptured microcapsules 130. One or both of the bodies preferably has the conformation of a sheet, and one or both is preferably transparent, so that color formation attributable to microcapsule rupture can be observed (through the transparent body or portion of a body) by viewing the exterior of the device.

In a preferred embodiment, both bodies are transparent sheets (or a single sheet, folded upon itself) of a polymeric material such as a polyester (e.g., MYLAR®) brand biaxially-oriented polyethylene terephthatate) having microencapsulated color former interposed between the sheets in an overlapping portion. In at least one region of the device, the overlapping portion formed between the sheets has dimensions such that the distance between the opposed sheets is much smaller (i.e., 10, 20, 50, 100, or 500 or more times smaller) than the minimum dimension of the overlapping portion, measured in lateral directions (i.e., perpendicular to the shortest distance between the opposed sheets). Of course, this relation need be true for only some of the overlapping portion—there can be other parts of the overlapping portion for which this relationship does not hold, but those other parts may not demonstrate the functionality described herein. It is sufficient if only apart of the overlapping portion has this conformation.

Numerous technologies for making pressure-sensitive microcapsules between two bodies are known, and substantially any or all of those technologies can be used to make the microcapsule-containing device described herein. Non-limiting examples of such technologies are described in U.S. Pat. No. 3,447,945 (Mishima et al.), U.S. Pat. No. 4,002,060 (Ogata et al.), U.S. Pat. No. 4,078,423 (Ogata et al.), U.S. Pat. No. 4,098,114 (Asao et al.), and U.S. Pat. No. 4,761,397 (Higashi et al.), Likewise, numerous methods of reliably associating an indicating device with food samples undergoing processing are known (e.g., devices and mechanism for adhering, tying, bundling, hanging, wrapping, stuffing, mixing, interleaving, or co-packaging devices and foodstuffs on, to, from, or with one another or on, to, from, or with common racks, packages, pallets, and the like) and can be used to reliably associate the device described herein with one or more foodstuffs for co-processing in an HPP method.

Advantageously, the devices and methods described herein provide convenient, preferably direct visual, confirmation that a foodstuff subjected to a HPP method has been subjected to the desired ambient pressure. That confirmation ability reduces the need for cumbersome and expensive methods of providing traffic control for HPP-treated foodstuffs.

DEFINITIONS

As used herein, each of the following terms has the meaning associated with it in this section.

A "foodstuff" is an item or article that is edible (including drinkable) by an animal such as a human or is useful as an ingredient for making an edible item or article. Non-limiting examples of foodstuffs include fruits, juices, vegetables, grains, flours, animal milks, yogurts, sweetened beverages, cuts of meat, and processed foods.

Two articles subjected to an HPP operation are "reliably associated" if the association between the two articles can be expected not to be disrupted by subjecting the reliably associated articles to the HPP operation. Non-limiting examples of such reliable associations include adhering one article to another, tying the two articles together, containing both articles in a container, affixing one article to a container used to contain the other article, and laminating one article in a portion of a packaging material used to enclose the other article.

The "average separation distance" between two opposed surfaces is, in the case of two perfectly flat, parallel surfaces, simply the distance between the parallel surfaces. In the case of substantially flat surfaces that are roughly parallel to one another, the average separation distance is the mean value of the shortest distance between individual points on one surface and the nearest portion of the other surface, averaged over the overlapping portion of the two surfaces.

The "minimum lateral dimension" of an overlapping region between two opposed, substantially parallel surfaces, is the shortest linear distance, measured in the plane of parallelism between the edges of the overlapping region. Relatively narrow portions of overlapping regions can be ignored for the purposes described herein, and the minimum lateral dimension considered for only broader regions. By way of example, for an overlapping region having the shape of a relatively large circle having a relatively thin "thread" extending therefrom, the minimum lateral dimension of the circle portion alone can be considered the minimum lateral dimension, which would be the diameter of the circle.

A "color former" is a chemical compound which either i) exhibits optical properties such that its presence can be discerned by the human eye or ii) is capable of reacting with a color developer to form a compound which exhibits optical properties that can be discerned by the human eye.

A "color developer" is a chemical compound which reacts with a color former to form a compound which exhibits optical properties that can be discerned by the human eye.

The "compressive bursting strength" of a microcapsule is the amount of force that must be applied to the microcapsule, when compressed between two parallel rigid sheets, in order to cause sufficient breakage of the microcapsule that liquid can flow between the interior of the microcapsule and the environment surrounding the microcapsule.

The unit "mils" is used in its art-accepted sense, i.e., thousandths of an inch.

Detailed Description

This disclosure relates to a pressure sensor device for use together with one or more foodstuffs in a HPP method.

Foodstuff-Sensor Assemblies

In an important embodiment, the disclosure relates to an assembly for indicating achievement of a selected ambient pressure in a HPP method for treating a foodstuff. The assembly includes the foodstuff reliably associated with the pressure sensor device described herein, as shown in FIG. 5.

HPP equipment typically uses a working fluid, most commonly water. Such equipment typically includes a pressure chamber into which a foodstuff is placed. After loading (i.e., placement of the foodstuff within the pressure vessel), the chamber is filled with the working fluid, and the chamber is pressurized by application of a high hydrostatic pressure (e.g., 200-1000 MPa, more typically 200-600 MPa) to the working fluid.

Because pressure within a fluid in a chamber is uniform throughout the fluid, and because the working fluid in an operating HPP apparatus completely surrounds the foodstuff, the hydrostatic pressure within the chamber is applied isotropically (i.e., not in any particular direction more than another) to the foodstuff. So long as the foodstuff does not contain compressible materials (e.g., gases such as air bubbles; water and other fluids tend to be substantially incompressible at HPP pressures), the shape of the foodstuff tends not to be altered significantly (even though some microscopic changes may occur, such as denaturation of proteins within the foodstuff). Furthermore, foodstuffs that do not include portions capable of withstanding deformation at the applied pressure will also transmit the pressure within the foodstuff, the result being that the hydrostatic pressure applied to the chamber occurs throughout the treated foodstuff.

Maintenance of the foodstuff at the applied pressure results in damage to microorganisms (e.g., bacteria, molds, yeast, and parasites) that may be present on or within the foodstuff. Regardless of the precise nature of the damage, microorganisms (other, perhaps, than bacterial spores) subjected to HPP treatment appear to replicate and metabolize at substantially tower rates than non-HPP-treated microorganisms. This effect is the primary basis for the desirability of HPP treatment of foodstuffs.

The Pressure Sensor Device

The pressure sensor device described herein includes two bodies (herein designated abase 110 and a sheet 120) and a plurality of microcapsules 130. Each of the base 110 and the sheet 120 is substantially impermeable to the working fluid, is deformable at the selected ambient pressure, and bears a matching opposable portion. The matching opposable portions 112 and 122, respectively, of the base 110 and sheet 120 closely fit one another when configured in an opposed configuration (i.e., the matching opposable portion 112 of the base 110 abutted against the matching opposable portion 122 of the sheet 120); preferably each is a substantially flat portion.

In the operable device, the opposable portions 112 and 122, respectively, of the base 110 and sheet 120 are disposed in a substantially parallel, opposed conformation defining an overlapping region 125. The overlapping region 125 is characterized by an average separation distance and lateral dimensions, meaning dimensions measured generally along the opposable portion surfaces. For example, in the case of a base 110 and sheet 120 each having a perfectly flat opposable portion (112 and 122, respectively) opposed to one another in a parallel fashion, the average separation distance is simply the shortest distance between the opposable flat portions and the lateral dimensions are the dimensions of the overlapping region 125 measured in directions perpendicular to that shortest distance. The average separation distance is significantly (i.e., at least 10, 20, 50, 100, or 500 or more times) smaller than the minimum lateral dimension of the overlapping region 125 for at least some portion of the overlapping region 125.

Contained within the overlapping region 125 (i.e., interposed between the base 110 and the sheet 120 in the overlapping region 125) is a plurality of microcapsules 130 that contain a color former. The microcapsules 130 are characterized by a compressive bursting strength (which may be a range of strengths for individual microcapsules 130 within the plurality) at which the color former will be released from within the microcapsules 130. If an anisotropic pressure greater than the compressive bursting strength of the microcapsules 130 is applied to the microcapsules 130 by the two faces of the overlapping region 125, then the color former be released and can be detected. For that reason, the compressive bursting strength of the microcapsules 130 in a device 100 used for detecting achievement of a selected ambient pressure should be not greater than (and preferably at least a little less than) that selected ambient pressure. The precise compressive bursting strength that should be used can be determined empirically and can, for example, be about half of the selected ambient pressure. Because pressurization apparatus often either fail or do not fail (i.e., they less commonly achieve only partial pressurization), the compressive bursting strength of the microcapsules 130 in the device 100 described herein can instead be simply selected to be significantly greater than atmospheric pressure, such as a value of 200, 125, 50, or 10 MPa.

The device can have other indicators (e.g., a temperature indicator or a moisture sensor) associated with it, so that the pressure-sensing functionality of the device can be combined with (for example) temperature- or moisture-sensing functionality.

The Base 110 and Sheet 120

The precise shapes and conformations of the base 110 and sheet 120 are not critical. However, some embodiments lend themselves to easier manufacture and assembly. For example, in one embodiment, the base 110 has the form of a second sheet (i.e., the device is composed of two sheets opposed against one another). The sheet 120 and the second sheet can have approximately the same thickness or different thicknesses, such as each being a plastic film having a thickness of about 2 to 50 mils.

The materials from which each of the base 110 and the sheet 120 are made is substantially immaterial, other than that each should be deformable at the ambient pressure for which detection is desired. By way of example, each of the base 110 and the sheet 120 can be a polyester film having a thickness of about 2 to 10 mils. Preferably, at least one of the base 110 and the sheet 120 is transparent.

At least one of the base 110 and the sheet 120 (preferably has a viewing portion adapted to permit detection of color former released from the microcapsules 130 by external visual observation of the device (i.e., not requiring disassembly of the device). Alternatively, the device can be disassembled to determine whether color former was released in the overlapping region 125. In a preferred embodiment, at least one of the base 112 and sheet 120 is sufficiently transparent or translucent that release of color former from the microcapsules 130 can be detected by direct visual observation of the viewing portion by an operator.

One or both of the base 110 and sheet 120 can act as a packaging material, or a component thereof, for containing a foodstuff. The base 110, sheet 120, or both can be an integral part of the packaging material (i.e., unitary with the packaging material such that removal of the base or sheet would compromise the integrity of the package to separate its interior and exterior), as shown for example in FIG. 6A, or it can be separable (e.g., tearable, detachable, or peelable) from the package, as illustrated for example in FIG. 6B, in which device 100 is integral with the package, but detachable therefrom (by tearing portion D from package P in FIG. 6B). If only one of the base and sheet is a part of a food package, the device is preferably configured such that no fluid communication between the microcapsule-containing overlapping portion of the device and the food-containing lumen of the package is possible when the package is intact. Such a configuration reduces the likelihood that microcapsules or their contents will contact a foodstuff within the package.

By way of example, a food package can include a roughly bowl-shaped container formed of a resilient, flexible plastic material (e.g., polyethylene or polyethylene terephthalate), a flexible plastic lidding sheet that seals a foodstuff within the concavity of the bowl-shaped container and acts as the base 110 of the device 110, and a relatively small, patch-shaped sheet 120 that overlaps at least a portion of the base 110, at an overlapping portion that contains microcapsules 130. The package can be filled with a foodstuff, sealed, and subjected to an HPP technique. If the ambient pressure in the HPP technique exceeds the compressive bursting strength of the microcapsules 130, they will burst and color former released therefrom can be viewed through the sheet 120, confirming operation of the HPP technique.

The Microcapsules 130

Figure 2:
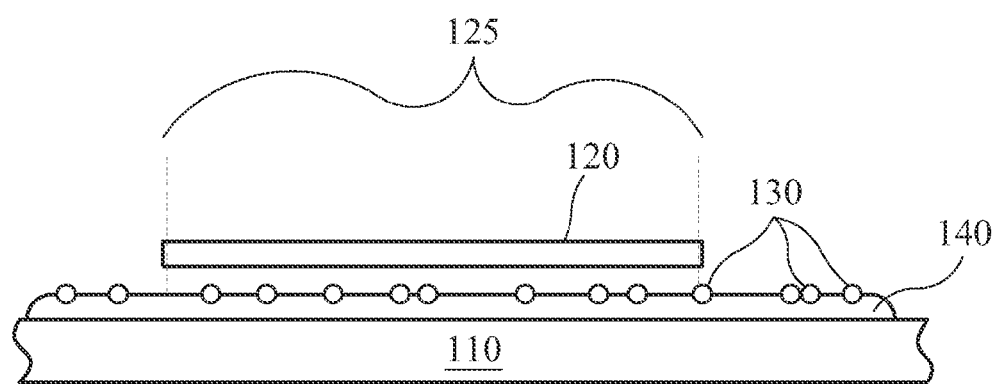
FIG. 2 is a cross-sectional diagram that illustrates one embodiment of the device described herein. In this embodiment, the sheet 120 covers less than all of the base 110, such that the overlapping region 125 includes the entire sheet 120 in this section, but less than the entire base 110. Microcapsules 130 are bound to the base 110 using a layer of a binder 140.

Methods and compositions for making microcapsules, including those containing solid and/or liquid reagents are well known, and substantially any such methods and compositions can be used to make the microcapsules 130 of the device described herein, subject to the limitations described herein. The precise location of the microcapsules 130 within the overlapping region 125 of the device is not material. The microcapsules 130 can, for example, be bound to the base 110 (e.g., as shown in FIG. 2), to the sheet 120 (e.g., as shown in FIG. 3), or to both, either directly or by way of a binding agent, such as a latex composition. Alternatively, the microcapsules 130 can be contained within, but not necessarily bound to any surface within the overlapping region 125, as shown in FIG. 1.

Non-limiting examples of suitable technologies for preparing microcapsules suitable for use in the devices described herein are found in U.S. Pat. No. 3,447,945 (Mishima et al.), U.S. Pat. No. 4,002,060 (Ogata et al.), U.S. Pat. No. 4,078,423 (Ogata et al.), U.S. Pat. No. 4,098,114 (Asao et al.), and U.S. Pat. No. 4,761,397 (Higashi et al.).

In one embodiment, one of the base 110 and the sheet 120 bears the microcapsules 130 and the other bears a color developer that reacts with the color former to generate a colored product upon release of the color former (e.g., as shown in FIG. 3). By way of example, the color former can be colorless or have a color different than (or less intense than) the colored product. In another embodiment, one of the base 110 and the sheet 120 bears the microcapsules 130 and the other is transparent and bears an absorbent material for absorbing the color former when it is released from the microcapsules 130 (e.g., as shown in FIG. 4). Of course, combinations of these technologies can be employed, such as an absorbent material having a color developer disposed thereon or suffused therein.

The microcapsules 130 can have a specified compressive bursting strength (e.g., one or more of 200, 124, 50, or 10 MPa, or any other desired value), or a range of compressive bursting strengths, as is known in the art. The compressive bursting strength can be selected, for example to be a fraction (e.g., half, 90%, 99%, or some other proportion) of the desired ambient pressure.

The device described herein can include microcapsules 130 that exhibit a range of compressive bursting strengths. By way of example, the microcapsules 130 can include some which burst at a relatively low (e.g., 40,000 psi) compressive pressure and some which burst at a substantially greater (e.g., 80,000 psi) compressive pressure, and the two populations of microcapsules can have the same or different color formers contained within them. Furthermore, the two populations can be disposed on the same portion of the device or in different portions. In one embodiment, the device includes several populations of microcapsules 130, each having a characteristic range of compressive bursting strengths and being disposed in an arrangement that facilitates observation of their bursting, such as by arranging the populations sequentially in order of increasing compressive bursting strength and by including indicia on or within the device that correlates color formation in one of the sequentially-ordered areas with a pressure.

Sheath

For safety or aesthetic reasons, it can be desirable to prevent contact between elements of the pressure sensor device and foodstuffs, either directly or through common contact with the working fluid of HPP method. Furthermore, the working fluid can interfere with at least some embodiments of the device (e.g., where operability of the device depends on the presence of air within the overlapping region, contact between the device and water of an HPP device can lead to displacement of air from the device by capillary or "wicking" action by which water can be drawn by its surface tension within the overlapping region. In such instances, it can be desirable to prevent contact between the device and the working fluid by ensheathing the device within a material that is substantially impermeable to the working fluid.

A wide variety of suitable sheathing materials are known (e.g., any of a variety of waterproof and water-resistant plastic films in the case of aqueous working fluids). Substantially any such sheathing material can be used. By way of example, the device can be laminated between heat-sealed polymeric sheets using known methods. The sheath can be evacuated if it is desired that substantially no gas (or very low pressure gas, such as 0.1 bar or less) occur within the sheath, or it can be filled with a selected fluid (e.g., a particular gas or liquid). Gas can also be substantially removed from between sheets by pressing (at a pressure less than the compressive bursting strength of the microcapsules) the sheets together during lamination, for example.

If the sheath is intended to shield its contents from the working fluid of an HPP operation and the sheath is sealed and contains a gas or other compressible fluid, then the dimensions and construction of the sheath should be selected such that compression of the fluid within the sheath at the HPP operating pressure wilt not cause rupture of the sheath.

Use of the Assembly

The pressure sensor device described herein can be used in method of confirming achievement of a selected ambient pressure in an HPP method for treating a foodstuff. The method includes the steps of reliably associating the foodstuff with the pressure sensor device, subjecting the foodstuff to the HPP process, and thereafter visually observing the viewing portion of the device. Visual detection of color former at the viewing portion confirms that the selected ambient pressure was achieved during the HPP process.

The device can be reliably associated with a single foodstuff (e.g., a head of lettuce) or package (e.g., as shown in FIG. 6) or with a plurality of foodstuffs or packages (e.g., a pallet of single-serving sliced-fruit pouches). The method by which the device and the foodstuff(s) are reliably attached is not critical. Substantially any method of association that will retain association of the device and foodstuff(s) during HPP treatment can be used. By way of-limiting example, the device can simply be placed loose in the pressure chamber of an HPP device and left there with the foodstuff until dissociation is desired. However, it is typically preferable that an indicator of appropriate HPP processing remain associated with the foodstuff(s) after they have been removed from HPP equipment. To achieve this end, the device and foodstuff(s) can be associated in any way and using any devices typically used in the food processing industry. By way of non-limiting examples, the device can be glued, tied, or otherwise attached to the foodstuff or package or to a container or rack that contains it (e.g., as shown in FIG. 7). The device can be co-packaged with the foodstuff or used to seal a package or container containing the foodstuff, such that the foodstuff cannot be removed from the package or container without removing or breaking the device. Likewise, the device can be part of, or contained within, a package used for commercial shipment, display, or sale of foodstuffs. By way of example, the device can be sandwiched between two layers of flexible plastic film that are used to seal a foodstuff for retail sale. In such an arrangement, the device is preferably sealed in a compartment distinct from (not fluidly communicable with) the compartment in which the foodstuff is sealed.

By reliably associating the device and the foodstuff, the information displayed by the device (i.e., whether or not proper HPP pressure was attained) can remain associated with the foodstuff and inform downstream users (i.e., customers, food processing plant workers, or retailers) of the foodstuff regarding the HPP status of the foodstuff.

Proposed Theory of Operation

Without being bound by any particular theory of operation, it is believed that the following explanation may be applicable to the observed operability of the pressure sensor device described herein.

Ambient pressure surrounding a sphere maintained in a fluid atmosphere tends to be equal on all surfaces of the sphere (absent fluid flow or other transitory phenomena), regardless of the ambient pressure of the atmosphere. Such isotropic pressure will not tend to deform or crush the sphere. Only when anisotropic (greater in one direction than another) pressure is applied to the sphere will the sphere be deformed. By way of example, a grape can be crushed between two fingers upon (anisotropic) application of force to two opposite ends of the grape. However, even when hundreds of megaPascals of pressure are isotropically applied to a grape (e.g., in an HPP system), the grape can remain visibly unchanged (not crushed).

Similarly, a microcapsule containing a color former (other than a gaseous color former or another compressible substance) should remain substantially unaltered upon application of isotropic pressure of substantially any magnitude, including pressures characteristics of HPP systems. Only if anisotropic pressure difference exceeding the compressive burst strength of a microcapsule is applied to a microcapsule should release of the color former therefrom be expected.

As described in the example, it was observed that color former-containing microcapsules interposed between two bodies having closely opposed surfaces in a device will release the color former upon increasing the ambient pressure surrounding the device, at least when the distance between the opposed surfaces is much smaller than the lateral dimensions of the overlapping region formed by the opposed surfaces.

That observation indicates that anisotropic pressure was applied to microcapsules within the overlapping region of the device, and that the anisotropic pressure occurred during ambient pressurization for the device. It is believed that the relative "thin-ness" (i.e., very small average separation distance relative to lateral dimensions) of the overlapping region that contained the microcapsules led to anisotropic pressurization of the microcapsules, resulting in their bursting or crushing. It is believed that compression of microcapsules caused by pressurization-induced displacement of the opposed surfaces 112 and 122, respectively, of the base 110 and sheet 120 towards one another in the overlapping region occurred more quickly than the corresponding pressurization-induced rise in pressure of the medium surrounding the microspheres within the overlapping region. It is immaterial whether this phenomenon occurred based on the compressibility of the fluid (e.g., a gas such as air) within the overlapping region or a lag between propagation of a pressure wave laterally from the edges of the overlapping region toward its center. In either event, the outcome is the same: microcapsules within the overlapping region are subjected to anisotropic pressure of sufficient magnitude to overcome their compressive bursting strength, and they burst, releasing color former.

The space between the sheet 120 and the base 110 is believed to be initially filled with air for commercially-obtained pressure sensitive two-layer film products such as PRESCALE brand film available from Fujifilm, Ltd. (Tokyo, Japan), or PRESSUREX brand film available from Sensor Products Inc. (Madison, N.J.), or other retailers. Application of a vacuum to such films using typical vacuum devices such as vacuum pumps and manifolds can evacuate most of the air from the microcapsule-containing space, such that the pressure drops to a few tenths or hundredths of a bar. Thus, evacuated films have approximately atmospheric pressure urging the two sheets together. So long as the microcapsules have a compressive bursting strength greater than atmospheric pressure, the capsules will not burst upon evacuation of a container containing the film. However, if the film is placed in a seated, evacuated container and subjected to an HPP technique, it is to be expected that the pressure exerted upon the container by the HPP working fluid will further compress the remaining gas between the sheet 120 and the base 110, resulting in application of the HPP working fluid pressure against the two sheets, which will burst interposed microcapsules if the HPP working fluid pressure exceeds the compressive bursting strength of the microcapsules. By way of example, if the compressive bursting strength of a microcapsule is 10 bars, complete evacuation of the space between the sheet 120 and the base 110 of a film in a sealed evacuated flexible container would be expected to result in pressure of about 1 bar on the microcapsules, and application of an additional 9+ bars of pressure upon the container by a working fluid would be expected to result in bursting of the microcapsules. Similarly, if the compressive bursting strength of the microcapsule is 5000 bars in the same apparatus, application of 4999+ bars of pressure would be expected to be required to achieve bursting of the microcapsules.

In devices in which at least a portion of the overlapping region is filled with air or another compressible fluid and contains microcapsules, the device is preferably configured such that the average separation distance between the base and sheet in that portion upon compression (or expulsion, or both) of the fluid at the selected ambient pressure (e.g., the minimum pressure for which sensing is desired) is less than the average diameter of at least some of the microcapsules. This configuration leads to anisotropic exertion of force upon the microcapsules that have a diameter greater than the distance between the adjacent base and sheet (or any materials layered upon either) when the ambient pressure on the exterior of the device either compresses the fluid or induces its expulsion from between the base and sheet. When that anisotropic force exceeds the compressive bursting strength of the microcapsule, the capsule will burst, releasing any color former contained therein and signaling achievement of the desired ambient pressure.

EXAMPLE 1

Use of a Microcapsule-Containing Pressure-Sensitive Bilayer Film as a Pressure Indicator in HPP The subject matter of this disclosure is now described with reference to the following Example. This Example is provided for the purpose of illustration only, and the subject matter is not limited to this Example, but rather encompasses all variations which are evident as a result of the teaching provided herein.

In order to test whether a microcapsule-containing pressure sensing device as described herein can be used as a pressure sensor for HPP, a commercially available microcapsule-containing, pressure-sensitive product was obtained and tested in a model HPP system.

PRESSUREX® brand tactile pressure indicating sensor film is available from Sensor Products, Inc. of Madison N.J. PRESSUREX film is a MYLAR-based bilayer film that has a color-forming reagent encapsulated within microcapsules fixed to a face of a polyester film. That face is opposed against a face of a second polyester film having a color-developing reagent thereon. When pressure is applied to the bilayer "sandwich" in the direction perpendicular to the plane of the films, the pressure is transmitted to the opposed faces of the two films. If the pressure is sufficiently great to burst some or all of the microcapsules, the color-forming reagent is released therefrom, contacts and reacts with the color-developing reagent, and forms a colored product which can be visually detected, either by ocular observation or more quantitative spectroscopic or digital-image-processing technologies. If the pressure is not sufficiently intense to burst the microcapsules, no color is developed. By varying the composition and construction of the microcapsules in controlled ways known in the art, pressure-sensitive films having various selected threshold pressures for color generation an be made.

Detection of such unidirectional application of force/pressure is a well-known use for pressure-indicating films such as PRESSUREX and is, in fact, the use for which such films are typically marketed. In order to translate the anisotropic pressure present within an HPP apparatus into a unidirectional-pressure/force, the pressure would need to be applied to only one face of a surface (e.g., to only one face of the a unidirectional-pressure-sensitive film, as was done in European patent application publication number EP 2116481, in which such a film was attached to a rigid base that does not deform at pressures characteristic of HPP systems). Just as liquidfined food products (e.g., grapes and other fruits and vegetables) are not crushed when subjected to HPP, a skilled artisan in this field would expect that the liquid-filled microcapsules of PRESSUREX and other microcapsule-containing, pressure-sensitive films would not be crushed when subjected to HPP (since pressure would be expected to be essentially equally applied to all surfaces of the microcapsule. The applicants have surprisingly discovered that this is not uniformly so.

In the experiments described in this example, a roughly rectangular piece of PRESSUREX brand pressure-sensitive film ("Super High" sensitivity) having dimensions of about 1.5 inches by 0.5 inch and having a color-generating pressure threshold value of about 18,500-43,000 psi (ca. 130-300 MPa, as reported by the supplier) was subjected to pressure characteristic of HPP systems. The film strip was taped using a commercial cellophane tape to the interior of a flexible plastic pouch. The pouch was evacuated and sealed using a commercial vacuum sealing device. The film-containing, evacuated pouch was placed within the pressure of a commercial HPP device, which was pressurized and then depressurized to observe the effect on the film.

When the pressure was increased to about 11,000 psi (ca. 75 MPa) and then returned to atmospheric pressure, no or substantially no color change was observed in the film. When the pressure was increased to about the minimal pressure threshold value of the film (ca. 18,500 psi, ca. 130 MPa) and then returned to atmospheric pressure, color change within the film was observable. At higher pressures, greater degrees of color development were observed, except that at pressures 40,000 psi (ca. 275 MPa) and greater, maximal color generation (as assessed by direct visual observation of the film) appeared to be achieved. That is, the color of the film pressurized to 87,000 psi (ca. 600 MPa) was visually indistinguishable from the film pressurized to 40,000 psi.

It was observed that portions of the PRESSUREX tape that were covered with cellophane tape (SCOTCH brand acetate-based adhesive tape, available from 3M, Maplewood, Minn.), used to secure the film to the interior of the vacuum sealed plastic pouch, did not develop color, even when subjected to pressure in an HPP system that induced coloration of the other portions of the film. Without being bound by any particular theory of operation, it is believed that this effect may be attributable to a 'cushioning' effect whereby adhesive between the acetate film of the SCOTCH brand tape was resiliently deformed around portions of the PRESSUREX film having microcapsules interposed between the sheets in the PRESSUREX film, thereby reducing compressive pressure applied to the microcapsules themselves, instead applying pressure more uniformly about the microcapsule. Thus, the resiliently deformable adhesive in SCOTCH brand tape may have reduced both the magnitude and the degree of anisotropy of pressure applied to microcapsules in the PRESSUREX tape, thereby permitting the microcapsules to remain intact at pressures at which they would burst in the absence of the SCOTCH brand tape adhesive. These observations indicate that the compressive bursting strength of microcapsules interposed between a body and a sheet in the device described herein can be effectively increased by including a layer of resiliently deformable material either i) between at least one of the body and the sheet and the exterior face of the device or ii) between the body and the sheet, whether or not the microcapsules contact (or are embedded within) the resiliently deformable material.

From the observations described in this example, it was concluded that the commercially-available film was suitable for detection of pressurization in HPP systems, at least pressurization to the minimal pressure threshold value of the film. It was recognized that various commercially-available pressure detection films can be substituted in place of the PRESSUREX film used in these experiments. It was furthermore recognized that films (or other configurations of a sheet and body) having interposed microcapsules having various selected compressive bursting strengths can be made using methods known in the art.

When the film piece was removed following pressure treatment, it was apparent that the color-forming reagent had been released from microcapsules within the film, because color had developed across most or all of the film. This was interpreted as an indication that an anisotropic pressure exceeding the pressure threshold of the film had been achieved at the colored portions of the film. This was furthermore interpreted as an indication that the film can be used as an indicator of pressure achievement in HPP systems—even if the film is not fixed to a rigid base, as in European patent application publication number EP 2116481.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A pressure sensor device for indicating achievement of a selected ambient pressure in a high pressure process for treating a foodstuff using a working fluid, the device comprising the a base, a sheet, and a plurality of microcapsules, each of the base and the sheet being substantially impermeable to the working fluid, being deformable at the selected ambient pressure, and bearing a substantially flat portion;

the substantially flat portions of the base and sheet being disposed in a substantially parallel, opposed conformation defining an overlapping region having lateral dimensions and an average separation distance, the plurality of microcapsules being interposed between the base and the sheet in the overlapping region;

the microcapsules containing a color former and having a compressive bursting strength less than the selected ambient pressure; and at least one of the base and the sheet having a viewing portion adapted to permit detection of color former released from the microcapsules by external visual observation of the device, whereby when the device is subjected to the selected ambient pressure, at least some microcapsules in the overlapping region burst, the color former is released from the microcapsules, and release of the color former can be detected by external visual observation of the device.

2. The device of claim 1, wherein at least a fraction of the microcapsules are disposed within a portion of the overlapping region that contains a compressible fluid.

3. The device of claim 2, wherein the fluid is air.

4. The device of claim 1, wherein the base has the form of a second sheet.

5. The device of claim 4, wherein each of the base and the sheet is a polyester film having a thickness of about 2 to 10 mils and at least one of the base and the sheet is transparent.

6. The device of claim 1, wherein the microcapsules are bound to the base.

7. The device of claim 1, wherein the microcapsules are bound to the sheet.

8. The device of claim 1, wherein the compressive bursting strength of the microcapsules is not more than 200 megaPascals (MPa).

9. The device of claim 1, wherein one of the base and the sheet bears the microcapsules and the other bears a color developer that reacts with the color former to generate a colored product.

10. The device of claim 1, wherein one of the base and the sheet bears the microcapsules and the other is transparent and bears an absorbent material for absorbing the color former when it is released from the microcapsules.

11. The device of claim 1, wherein the average separation distance is at least 100 times smaller than the minimum lateral dimension of the overlapping region.

12. The device of claim 1, wherein the device has a portion adapted to be reliably associated with a plurality of foodstuffs.

13. The device of claim 12, wherein the portion is adapted to be reliaby associated with a rack that holds the plurality of foodstuffs.

14. The device of claim 13, wherein the foodstuffs cannot be removed from the rack without displacing the device from the rack when the portion is associated with the rack.

15. The device of claim 1, wherein the device has a portion adapted to be reliably associated with a package that contains the foodstuff.

16. The device of claim 15, wherein the package is selected from the group consisting of a flexible bottle and a flexible pouch.

17. The device of claim 1, being sealed within a sheath that is substantially impermeable to the working fluid.

18. The device of claim 17, wherein the sheath is substantially evacuated.

\* \* \* \* \*